United States Patent
Gooβen et al.

(10) Patent No.: US 9,907,518 B2
(45) Date of Patent: Mar. 6, 2018

(54) X-RAY IMAGING GUIDING SYSTEM FOR POSITIONING A PATIENT

(71) Applicant: KONINKLIJKE PHILIPS N.V., Eindhoven (NL)

(72) Inventors: André Gooβen, Radbruch (DE); Claire Levrier, Rueil-Malmaison (FR); Gereon Vogtmeier, Aachen (CR); Raoul Florent, Ville D'Avray (FR); Liesbet Hilde Hadewijch Roose, Hamburg (DE); Jens Von Berg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 697 days.

(21) Appl. No.: 14/358,808

(22) PCT Filed: Nov. 15, 2012

(86) PCT No.: PCT/IB2012/056458
§ 371 (c)(1),
(2) Date: May 16, 2014

(87) PCT Pub. No.: WO2013/072872
PCT Pub. Date: May 23, 2013

(65) Prior Publication Data
US 2014/0348296 A1    Nov. 27, 2014

(30) Foreign Application Priority Data

Nov. 18, 2011  (EP) ..................................... 11189668
Mar. 7, 2012  (EP) ..................................... 12305274

(51) Int. Cl.
*A61B 6/08* (2006.01)
*A61B 6/04* (2006.01)
(Continued)

(52) U.S. Cl.
CPC .................. *A61B 6/08* (2013.01); *A61B 6/04* (2013.01); *A61B 6/0492* (2013.01);
(Continued)

(58) Field of Classification Search
CPC ........... A61B 6/04; A61B 6/0492; A61B 6/06; A61B 6/08; A61B 6/4208; A61B 6/46;
(Continued)

(56) References Cited

U.S. PATENT DOCUMENTS 5,539,798 A * 7/1996 Asahina ................. A61B 6/022
348/E5.086
6,856,670 B2   2/2005 Hoheisel
(Continued)

FOREIGN PATENT DOCUMENTS

JP    10186045       7/1998
JP    2000350719 A * 12/2000
(Continued)

*Primary Examiner* — Glen Kao

(57) ABSTRACT

An X-ray imaging guiding system for positioning a region of interest of a patient for X-ray image acquisition includes an X-ray detector arrangement, and graphical positioning information. The graphical positioning information includes a graphical target anatomy representation. The graphical target positioning information is provided in spatial relation with the X-ray detector arrangement. The graphical target anatomy representation indicates a target position of a respective anatomy of the patient for a determined X-ray image acquisition. Further, the graphical positioning information is adaptable in accordance with the determined X-ray image acquisition.

19 Claims, 11 Drawing Sheets

(51) Int. Cl.
*A61B 6/00* (2006.01)
*G01T 1/20* (2006.01)
*A61B 6/06* (2006.01)

(52) U.S. Cl.
CPC .............. *A61B 6/4208* (2013.01); *G01T 1/20* (2013.01); *A61B 6/06* (2013.01); *A61B 6/46* (2013.01); *A61B 6/467* (2013.01); *A61B 6/542* (2013.01); *A61B 6/582* (2013.01); *A61B 6/589* (2013.01)

(58) Field of Classification Search
CPC ......... A61B 6/467; A61B 6/542; A61B 6/582; A61B 6/589; G01T 1/20

See application file for complete search history.

(56) References Cited

U.S. PATENT DOCUMENTS

| | | |
|---|---|---|
| 7,583,426 B2 | 9/2009 | Shin |
| 7,767,974 B2 | 8/2010 | Jung |
| 2008/0037711 A1 | 2/2008 | Peterfy et al. |
| 2008/0290280 A1 | 11/2008 | Ruetten et al. |
| 2009/0180590 A1 | 7/2009 | Borgmann et al. |
| 2009/0268865 A1 | 10/2009 | Ren |
| 2009/0283685 A1 | 11/2009 | Takeda et al. |
| 2010/0054417 A1 | 3/2010 | Nishino et al. |
| 2010/0198112 A1 | 8/2010 | Maad |
| 2011/0135190 A1 | 6/2011 | Maad |
| 2011/0249799 A1* | 10/2011 | Lalena ............... A61B 6/08 378/97 |

FOREIGN PATENT DOCUMENTS

| | | |
|---|---|---|
| JP | 2005296499 | 10/2005 |
| WO | WO2006038165 | 4/2006 |
| WO | 2011130210 A2 | 10/2011 |
| WO | WO2012121890 | 9/2012 |

* cited by examiner

X-RAY IMAGING GUIDING SYSTEM FOR POSITIONING A PATIENT

CROSS-REFERENCE TO PRIOR APPLICATIONS

This application is the U.S. National Phase application under 35 U.S.C. § 371 of International Application Serial No. PCT/IB2012/056458, filed on Nov. 15, 2012, which claims the benefit of European Applications Serial Nos. 12305274.8, filed on Mar. 7, 2012 and 11189668.4 filed on Nov. 18, 2011. These applications are hereby incorporated by reference herein.

FIELD OF THE INVENTION

The present invention relates to an X-ray imaging guiding system for positioning a patient for X-ray image acquisitions, an X-ray imaging system, a method for guiding in positioning a region of interest of a patient for X-ray image acquisition, as well as to a computer program element and a computer readable medium.

BACKGROUND OF THE INVENTION

In X-ray imaging, patient positioning is a necessity, for example, for minimum dose requirements. A region of interest of a patient, for example a certain organ or a certain region of an extremity, such as a foot or a hand, is placed and thus positioned by a technician. The region of interest is arranged such that the X-radiation will cover a region of interest as much as possible on the one hand, and while avoiding to expose the patient to unnecessary radiation on the other hand, i.e. radiation which radiates through regions that do not belong to the region of interest. Therefore, a light projection, for example, indicates the central point of the X-ray radiation, wherein a projection device is mounted to the X-ray source to visualize the surface area of the object, for example the patient, that will be radiated or hit by X-ray radiation. Besides the central point, also collimation is projected such that the area, which will be radiated, is visible to the technician. The technician then positions the patient according to the particular needs. WO 2006/038165 A1 describes the planning of imaging parameters in an X-ray system, wherein an optical image of the patient positioned in front of the detector is generated and displayed overlaid with imaging parameters. The patient can then be repositioned according to the displayed overlay. However, it has been shown that patient positioning can be challenging for technicians and requires time, and also staff members, which have to move between the location of the X-ray imaging system, and the location where the control interface for the X-ray imaging system is located, usually a separate room having only visual contact to the patient.

SUMMARY OF THE INVENTION

There may be a need to improve and facilitate positioning of a patient for X-ray image acquisitions.

The object of the present invention is solved by the subject-matter of the independent claims, wherein further embodiments are incorporated in the dependent claims.

It should be noted that the following described aspects of the invention apply also to the X-ray imaging guiding system, the X-ray imaging system, the method for guiding and positioning a region of interest of a patient for X-ray image acquisition, as well as for the computer program element and the computer readable medium.

According to a first aspect of the present invention, an X-ray imaging guiding system for positioning a patient for X-ray image acquisition is provided, comprising an X-ray detector arrangement and graphical positioning information. The graphical positioning information comprises at least a graphical target anatomy representation. The graphical target positioning information is provided in spatial relation with the X-ray detector arrangement. The graphical target anatomy representation indicates a target position of a respective anatomy of the patient for a determined X-ray image acquisition. The graphical positioning information is adaptable in accordance with the determined X-ray image acquisition.

The graphical target anatomy representation may be based on a stored model, which model is adapted to the determined X-ray image acquisition and/or the current patient.

The model can also be adapted based on patient's data provided by a patient data base.

An external body measurement arrangement may be provided and the model is adapted based on patient data thus acquired.

The graphical target anatomy representation may indicate outlines of an anatomic structure of a determined region of interest, for example, for assisting staff members, e.g. a medical laboratory scientist.

The graphical target anatomy representation may indicate outlines of at least a part of the body of a patient, i.e. the contour of the body, for example, for guiding the patient himself.

According to an exemplary embodiment, a projection arrangement for visible light projection is provided, and the graphical target anatomy representation is provided as a visible light projection in a projection direction towards the detector arrangement.

According to an exemplary embodiment, the graphical positioning information comprises a target indicator indicating a predetermined area of the detector, and the graphical target anatomy representation and the target indicator are provided in a predetermined spatial relation.

According to a further exemplary embodiment, a patient positioning arrangement is provided, detecting movement of the patient. The graphical target anatomy representation is linked to the movement of the patient. The target indicator is provided indicating a predetermined area of the detector, and the graphical target anatomy representation and the target indicator can be brought into a determined spatial relation, for example through the respective motion of the X-ray detector arrangement and the patient himself in relation to each other.

According to a further exemplary embodiment, the X-ray detector arrangement comprises a visible surface arranged such that it is located in a radiation beam during the X-ray image acquisition. The graphical positioning information is provided on the visible surface. The visible surface is provided at least as one of the group of: i) a detector cover; ii) a patient support surface; or iii) a patient abutting surface.

According to a further exemplary embodiment, the visible surface comprises an adaptable display surface.

According to an exemplary embodiment, the adaptable display surface is provided with an e-paper coating structure.

According to an exemplary embodiment, the adaptable display surface is light emitting, and a light emitting layer with at least one light emitting element is arranged in front of a detector photodiode layer.

According to a further exemplary embodiment, light emitting elements and detector photodiode elements are arranged in an interlaced pattern as a mixed layer.

According to a further exemplary embodiment, the at least one light emitting element is provided as an organic light-emitting diode (OLED).

According to an example, the detector layer can be provided with organic material. For example, in case of a mixed layer with OLED for the light emitting elements, detector cells can be provided with organic elements as well.

According to an example, the adaptable display surface is provided with an organic light-emitting diode (OLED) coating structure.

For example, an OLED arrangement, being an active display, also provides an active light source that can be integrated into the examination-room's lighting concept. The OLED arrangement can, for example, enhance contrast and thus improve the patient's visual situation.

According to a further exemplary embodiment, the at least one light emitting element is provided as a reset light source for a scintillator of the detector arrangement.

According to a further example, the detector is configured to detect a reflected intensity from light provided by a light emitting adaptable display surface, and/or a visible light projection from a projection arrangement. The X-ray imaging guiding system is further configured to determine an actual field of view after positioning of an object. For example, the actual field of view can be provided for an optimized setting of shutters and/or optimized tube settings.

According to a further exemplary embodiment, the graphical positioning information comprises instructions related to the determined X-ray image acquisition. The instructions are provided for an interaction of a user. The visible surface comprises areas or portions which are activatable by the user for entering feedback upon the instructions.

According to a further exemplary embodiment, the graphical positioning information is maintained during an X-ray imaging procedure.

According to a second aspect of the present invention, an X-ray imaging system is provided, comprising an X-ray source and a guiding system according to one of the above described X-ray imaging guiding systems. The X-ray source is configured to radiate an X-ray beam towards the detector arrangement. The graphical positioning information is provided for guiding in positioning a region of interest of a patient between the X-ray source and the detector arrangement for X-ray image acquisition.

According to a third aspect of the present invention, a method for guiding in positioning a region of interest of a patient for X-ray image acquisition is provided. The method comprises the following steps:
a) providing graphical positioning information, wherein the graphical positioning information comprises at least a graphical target anatomy representation;
b) displaying the graphical target positioning information in spatial relation with the X-ray detector arrangement, wherein the graphical target anatomy representation indicates a target position of a respective anatomy of the patient for a determined X-ray image acquisition.

The graphical positioning information is adaptable in accordance with the determined X-ray image acquisition, i.e. the set or planned image acquisition, or image acquisition procedure.

According to an exemplary embodiment, after positioning of an object, an actual field of view is determined by detecting a reflected intensity from light provided by a light emitting adaptable display surface, or by detecting a visible light projection from a projection arrangement.

According to an exemplary embodiment, the determined actual field of view is used for adapting the graphical positioning information, and an updated graphical target anatomy representation is provided and displayed in steps a) and b).

According to an aspect of the present invention, information for the exact positioning is provided in a straight forward manner, i.e. as a type of information that is directly understandable by the technician or staff member as well as by the patient himself. This information is provided in form of an image of the anatomy which gives the user an unambiguous impression for the correct position. In other words, intuitive information for the positioning is provided, for example in the exact location of the target position. Thus, instead of analyzing the position of a light cross indicating the central point of an X-ray beam, and to bring that central point in relation to a region of interest, the user, i.e. the patient or the technician, can simply align the anatomy of the patient with the image provided. The positioning information can be provided either as a projection onto the detector surface, or, in case the patient is already arranged in front of the detector surface, as a projection onto the patient's surface. The positioning information can also be provided directly on the detector surface, i.e. on the visible surface of the detector housing or other visible surfaces, for example by an e-paper coating. Since the positioning information is provided in a manner which does not affect the X-ray image acquisition itself, the positioning information can be provided throughout the image acquisition procedure. Thus, a technician can control the correct positioning even when being located in the control room by a visual feedback through a window usually provided between the two rooms. Of course, also a camera can be installed for providing the respective view from one room to the next room, where it is displayed on a monitor. The positioning information being available throughout the image acquisition thus improves the correct positioning and thus helps in avoiding unnecessary image acquisitions.

According to a further aspect of the present invention, the X-ray detector arrangement comprises an automatic exposure control device and the positioning information also indicates the respective automatic exposure control (AEC) device, for example an AEC chamber. For example, a lung model of a patient and the AEC chambers are optimally placed to each other and are thus displayed on the patient back, for example. In a different mode, the AEC chamber's position is displayed on the patient, indicating their position. Further, the anatomy of the patient is displayed, for example as outlines of lungs. This can be achieved, for example by a camera tracking the patient and an independent display, i.e. a display independent of the display of the AEC chambers. The technician or user has then to position the patient so that the AEC chambers are well-placed in the anatomy display.

According to a further aspect of the present invention, the patient positioning is facilitated such that the target anatomy is placed in front of a measurement chamber, and collimated as tightly as possible, to achieve comparable diagnostic quality, especially for follow-up studies. Besides facilitating the positioning for technicians, it is also possible to use the target positioning information such that the patients themselves or their relatives can carry out the positioning, for example in emerging markets. Thus, for certain examination type, patients can be lined up and radiographed with a very high throughput.

According to a further aspect, it is also possible to provide instructive information to have a sort of dialogue, or feedback, for guiding the patient, or the technician, through the positioning steps, and also the exposure steps. The positioning is self-explanatory to the examined patient, instructions can be provided as questions to be answered by clicking or pointing at certain regions of the surface, thus providing an interactive feedback with the patient.

These and other aspects of the invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
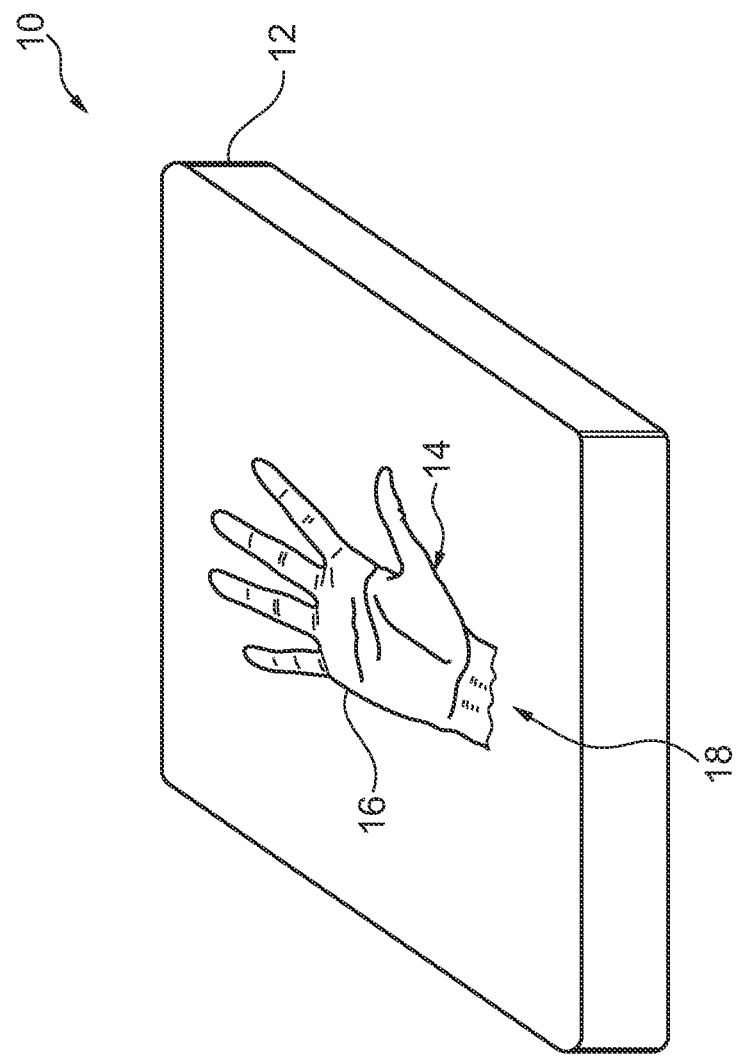
FIG. 1 shows an exemplary embodiment of an X-ray imaging guiding system for positioning a patient for X-ray image acquisitions according to the present invention.

FIG. 1 shows an X-ray imaging guiding system 10 for positioning a patient for X-ray image acquisitions. The X-ray imaging guiding system 10 comprises an X-ray detector arrangement 12 and graphical positioning information 14.

The graphical positioning information comprises at least a graphical target anatomy representation 16. As an example only, outlines of a human hand are shown as graphical target anatomy representation 16. The graphical target positioning information is provided in spatial relation with the X-ray detector arrangement 12. The graphical target anatomy representation 16 indicates a target position 18 of a respective anatomy of the patient for a determined X-ray image acquisition. The graphical positioning information 14 is adaptable in accordance with the determined X-ray image acquisition.

As already indicated above, the graphical target anatomy representation 16 can be based on a stored model, which model is adapted to the determined X-ray image acquisition and/or the current patient. The model can be adapted based on patient data provided by a patient data base. An external body measurement arrangement may be provided, and the model can be adapted based on the patient data acquired with such body measurement arrangement.

The graphical target anatomy representation 16 indicates outlines of anatomic structures of a determined region of interest, for example of an extremity such as a hand or a foot, or outlines of internal organ structures.

Figure 2:
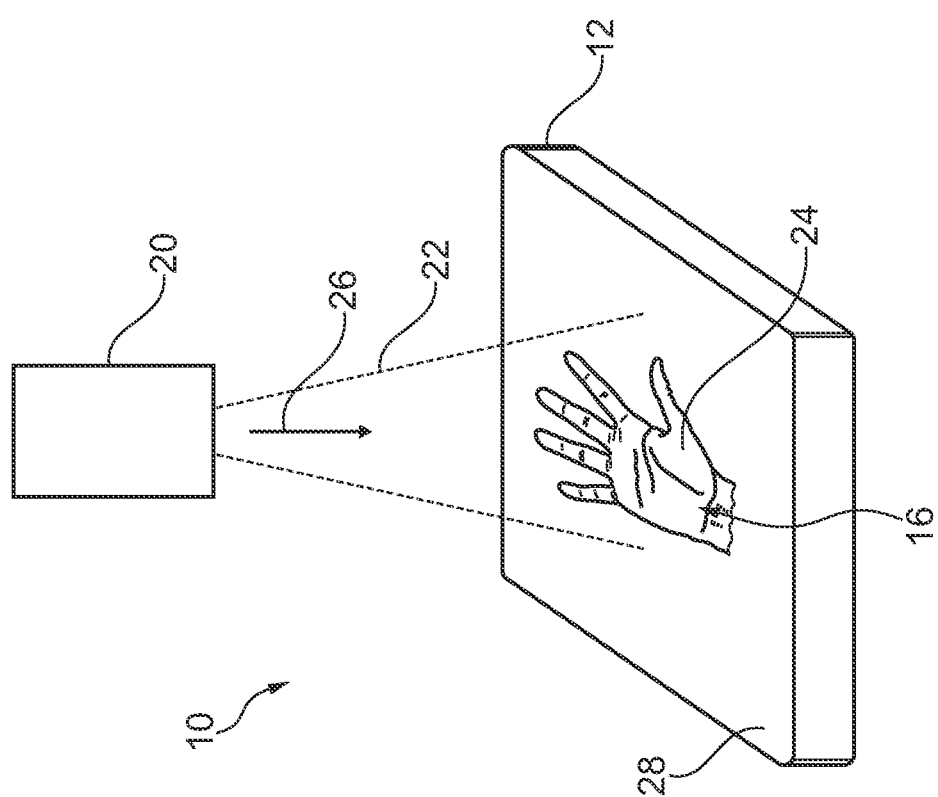
FIG. 2 shows a further exemplary embodiment of an X-ray imaging guiding system according to the present invention.

FIG. 2 shows a further exemplary embodiment of the X-ray imaging guiding system 10. FIG. 2 shows a projection arrangement 20 for visible light projection, indicated by two dotted lines 22. The graphical target anatomy representation 16 is provided as a visible light projection 24 in a projection direction 26 towards the detector arrangement 12.

For example, the visible light projection 24 is provided on a cover surface 28 of the detector arrangement 12. It must be noted that the detector arrangement 12 and its constructive setup are not further discussed here.

For example, the projection arrangement 20 comprises a light projector or a laser projector. The projection direction is aligned with an X-ray projection direction for the determined X-ray image acquisition. The term "aligned with" refers to a projection direction which can be the same as the X-ray projection direction, i.e. coincide. The term can also refer to a slightly inclined projection direction which hits the detector, or a patient's body surface, at a similar point compared to the X-ray projection direction.

Figure 3:
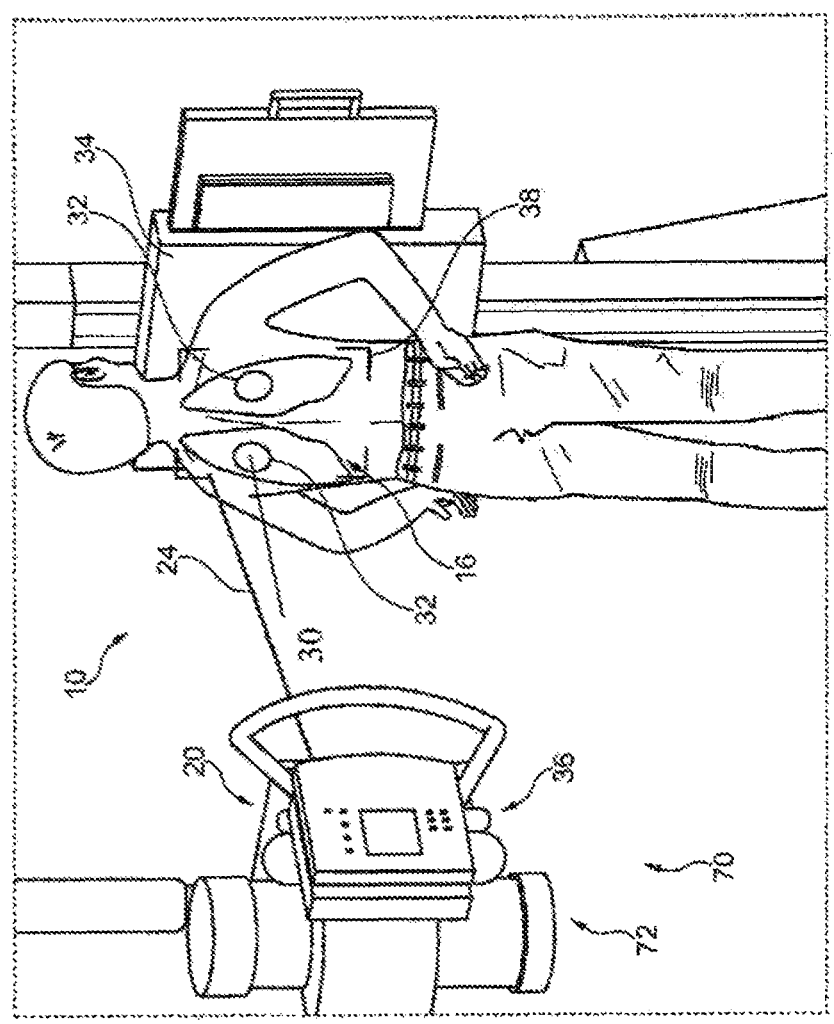
FIG. 3 shows a further exemplary embodiment of an X-ray imaging guiding system according to the present invention in an exemplary embodiment for an X-ray imaging system according to the present invention.

FIG. 3 shows a further example of an X-ray imaging guiding system 10, wherein the graphical positioning information comprises a target indicator 30 indicating a predetermined area of the detector. For example, the target indicator 30 indicates two chambers of an AEC device with respective circles 32. The graphical target anatomy representation 16, shown in form of the left and right lungs for example, and the target indicator 30 are provided in a predetermined spatial relation. Thus, the two circles 32 indicating the AEC chambers are shown in combination with the lung structure such that the AEC chambers relate to the respective position of the lungs to ensure proper automatic exposure control of the X-radiation.

The target anatomy representation 16 is provided as the above mentioned visible light projection 24, which, when the patient is positioned in front of a vertical detector arrangement 34, is projected on the patient's upper part of the body for a chest acquisition, for example. Of course, in case the patient is absent, the visible light projection 24 is projected onto the cover surface of the detector arrangement 34.

For example, the projection arrangement 20 can be provided integrally with an X-ray source arrangement 36, for example suspended from the ceiling.

The graphical positioning information 14 may also comprise an indication of the radiated area, for example by indicating boundaries 38, provided by shutters and/or wedges.

According to the example shown in FIG. 3, the target anatomy representation 16 and the target indicator 30 are shown in a fixed relation. The patient is accordingly positioned such that the projected target anatomy representation coincides with the (non-visible) lung structure of the patient himself Therefore, the patient can be moved sideward, or even upward and downward by an adjustable stand surface, for example. Of course, also the detector and source arrangement 34, 36 can be moved vertically for adjustment of the height, and the patient himself only moves sideward until the correct position for the X-ray radiation procedure has been found.

Figure 4:
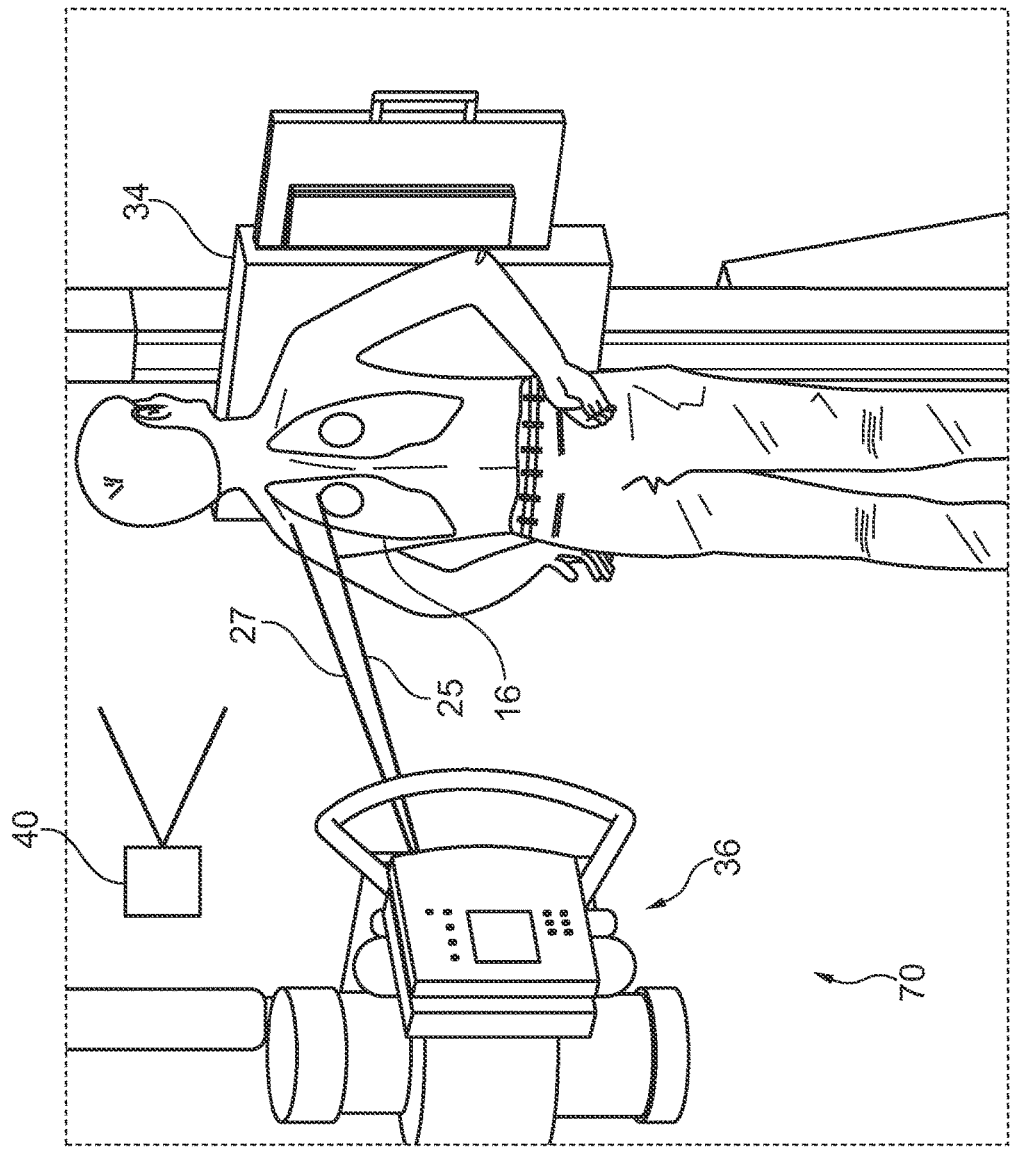
FIG. 4 shows a further exemplary embodiment of an X-ray imaging system with an X-ray imaging guiding system according to the present invention.

FIG. 4 shows a further embodiment of an X-ray imaging guiding system 10, wherein the graphical target anatomy representation 16 and the target indicator 30 are not having a fixed relation to each other. Rather, the target indicator 30 is provided indicating a predetermined area of the detector, and is thus being provided as a fixed projection.

Further, a patient positioning arrangement 40 is provided for detecting movement of the patient. The graphical target anatomy representation 16 is moved according to the movement of the patient. Thus, the target anatomy representation 16 is indicating the location of the (non-visible) lung structure of the patient. For a correct positioning, the graphical target anatomy representation 16 and the target indicator 30 can be brought into a determined spatial relation, such as by the respective motion or movement of the X-ray detector arrangement and/or the patient himself. For example, since the organ display follows the patient displacement, the user has to position the patient such that the AEC chambers, i.e. the target indicator 30, are well-placed in the anatomy display provided by the graphical target anatomy representation 16.

It must be noted that the patient positioning arrangement 40 is indicated schematically only. For example, it can be provided as a camera and the respective software for image analysis detecting the movement of the patient. In another example, the patient positioning arrangement 40 is provided with infrared or ultrasound sensors detecting the movement of the patient. It must be noted further, that the patient positioning arrangement 40 can be formed integrally with the X-ray source arrangement 36, or separately, as indicated in FIG. 4. It is further noted that the target indicator 30 is not necessarily only combined with upper chest exposures, but can be used with any other image acquisition concerning other regions of interest inside the body.

In FIG. 4, reference numeral 25 indicates a projection of the target indicator 30, and reference numeral 27 indicates a separate projection of the target anatomy representation 16.

The target anatomy representation 16 shown in combination with a target indicator 30, either in a fixed relation or in an adaptable relation, is assisting staff members, e.g. a medical laboratory scientist.

Figure 5:
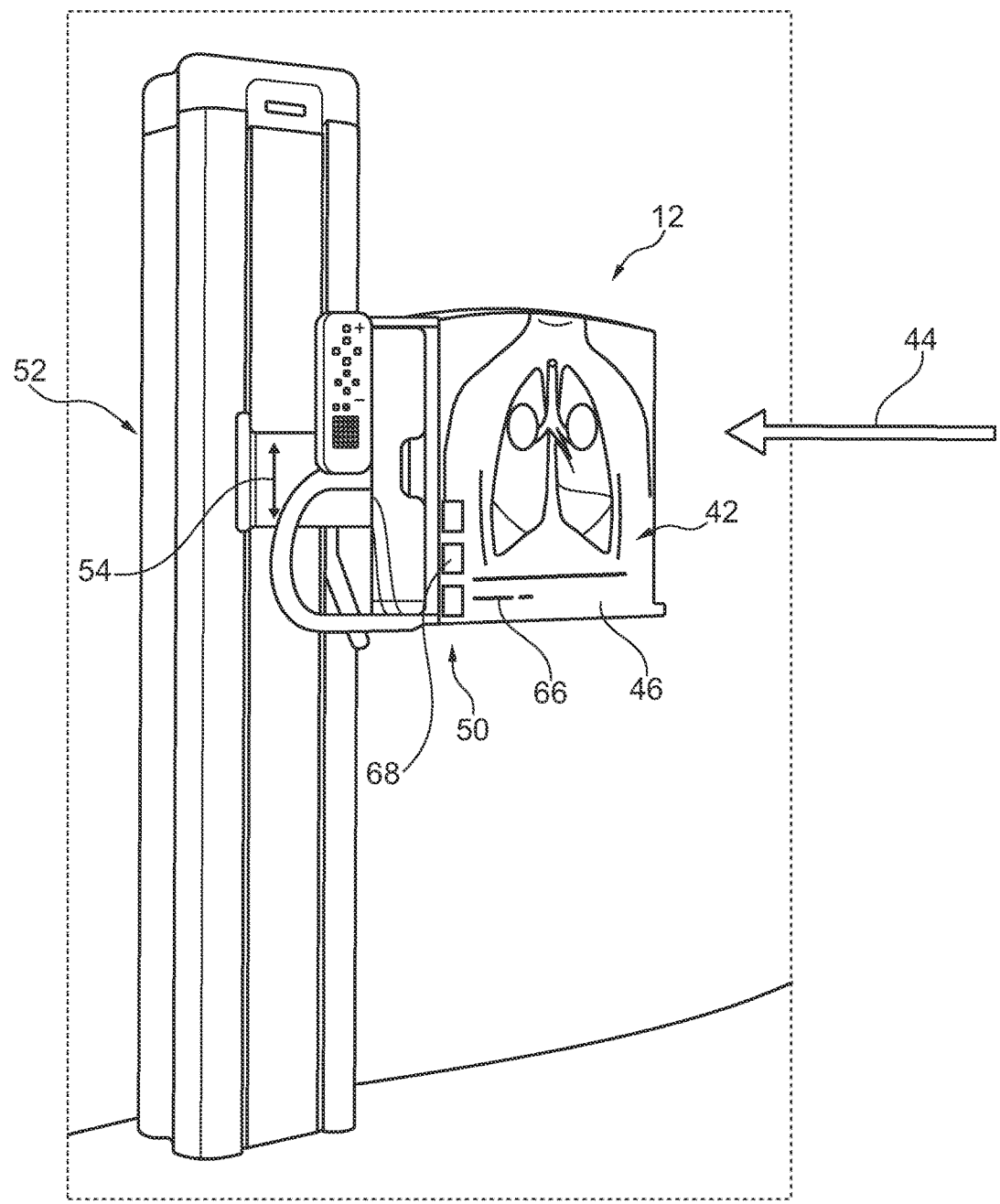
FIG. 5 shows a further exemplary embodiment of an X-ray imaging guiding system according to the present invention.

FIG. 5 shows a further example of an X-ray imaging guiding system 10 according to the present invention. The X-ray detector arrangement 12 comprises a visible surface 42 arranged such that it is located in a radiation beam, indicated with a symbolic arrow 44, during the X-ray image acquisition. For example, the visible surface 42 may be provided as a visible detector cover surface. However, also other visible surfaces can be provided, for example a separate surface in front of the detector. The graphical positioning information is provided on the visible surface 42.

The visible surface 42 is provided for example as a detector cover 46, as mentioned above. The visible surface 42 may also be provided as a patient support surface 48 (for example, see FIG. 6). The visible surface may also be provided as a patient abutting surface 50, for example for vertically arranged detectors, which are provided such that a patient can stand in front of the detector and abut on the abutting surface 50 for minimizing movement of the patient. It is noted that the term "detector cover 46" relates also to such cases where an abutting of a patient is not used, i.e. in cases where a patient is standing freely in front of a detector.

The visible surface comprises, for example, a patient table, a wall stand as a surface, against which the patient can lean or rest, or otherwise touch, a wall stand in front of which the patient stands without touching the surface. The visible surface comprises the visible surface of a detector housing, for example.

However, in any case the target position for the determined X-ray image acquisition of the respective anatomy of the patient is provided on the visible surface. For example, the graphical target anatomy representation 16 is provided on the visible surface 42.

The example shown in FIG. 5 shows an upright standing detector which is mounted to a motorized support 52 for allowing an up- and downward movement of the detector, as indicated with double arrow 54. An X-ray source, not further shown in FIG. 5, may then be provided for the actual X-ray image acquisition procedure.

Figure 6:
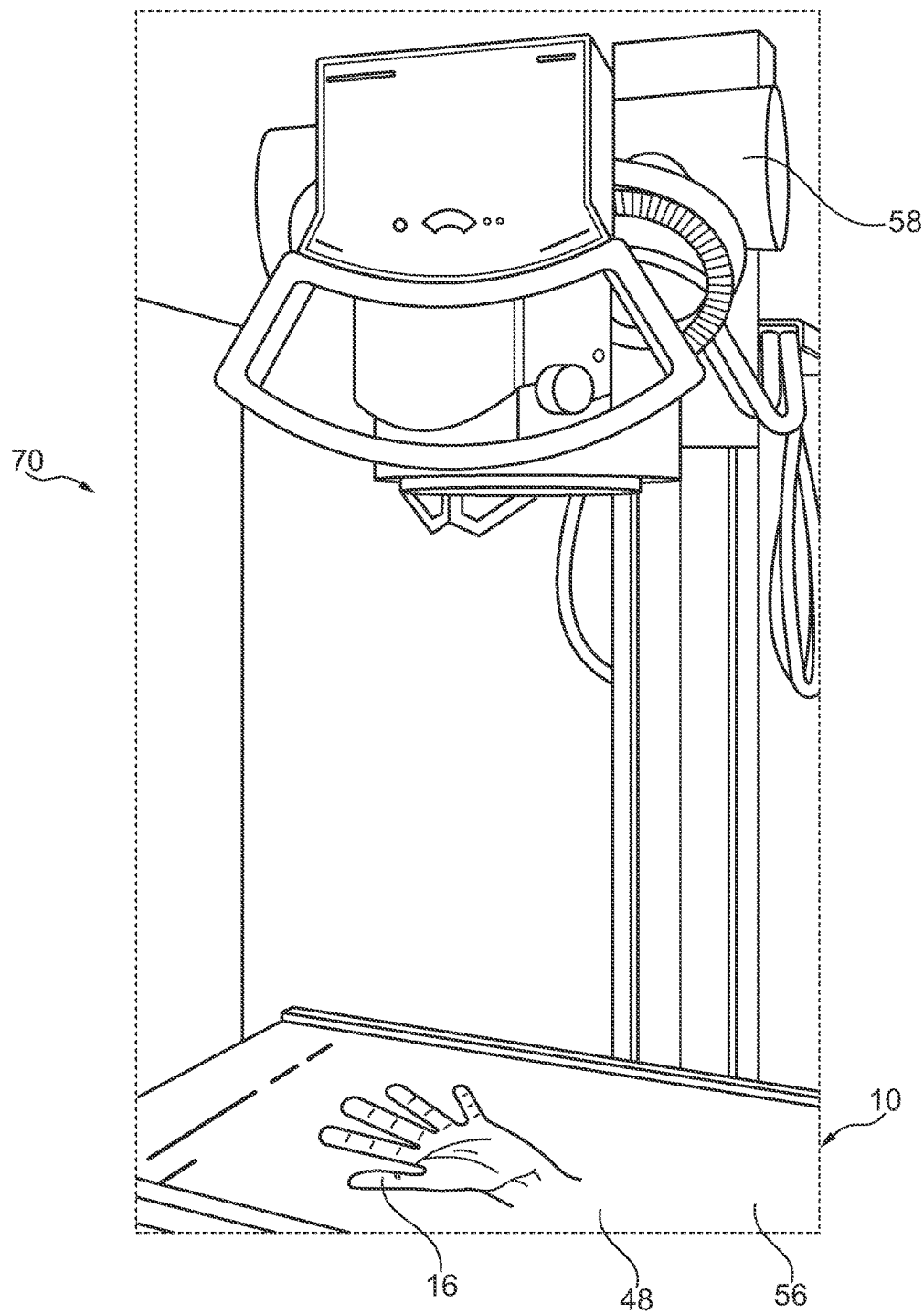
FIG. 6 shows a further exemplary embodiment of an X-ray imaging system with an X-ray imaging guiding system according to the present invention.

FIG. 6 shows the X-ray imaging guiding system 10 as a patient support 56 having the patient support surface 48. The target anatomy representation 16, shown as an example for a hand, is provided on the patient support surface 48. Further, an X-ray source arrangement 58 is shown above the patient support surface 48.

Figure 7:
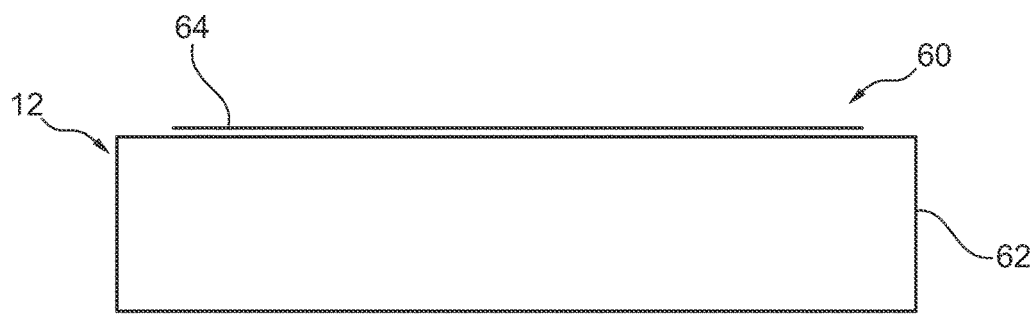
FIG. 7 shows an X-ray detector arrangement of an X-ray imaging guiding system according to an exemplary embodiment of the present invention.

According to a further example, the visible surface 42 comprises an adaptable display surface 60, as shown in FIG. 7. The visible surface 42 provided as the adaptable display surface 60 is arranged, for example, on top of a housing structure 62 of the X-ray detector arrangement 12. However, the adaptable display surface 60 can also be formed integrally with the housing structure 62, thus forming the upper surface of the housing structure.

The visible surface 42 may be provided as a graphical user interface. The adaptable display surface 60 is displaying the graphical target anatomy representation 16 (not further shown in FIG. 7).

The adaptable display surface 60 may be provided with an e-paper coating structure 64. As e-papers do not need constant power supply, information can be shown also when the system is not supplied with energy. E-papers are also applicable for mobile devices, in particular for detectors used in digital radiography, as mobile cassettes and portable, wireless detectors.

The term "visible surface" also relates to surfaces where the actual adaptable layer is arranged behind a cover or protector layer, the latter being the front surface for the user. However, the graphical target anatomy information is visible and thus shown on that front layer.

According to a further example (not shown), the graphical positioning information 14 is sequentially shown in an alternating manner with steps of image acquisition. For example, the positioning information is firstly provided for a period of time. Once the positioning has been completed, the positioning information is not shown anymore, but an image is acquired, i.e. one or several so-to-speak short X-ray shots are provided, which are of course not visible. Once the acquisition itself has been completed the positioning information shown again. In case of further images, these steps can be repeated, for example, in case of images under contrast agent injection.

According to a further aspect of the present invention, graphical positioning information 14 is maintained during at least a part of the image acquisition, preferably during the complete X-ray imaging procedure. For example, the graphical positioning information 14 is maintained visibly. The graphical positioning information 14 may be provided permanently, but can also be provided alternating with image acquisition steps in such a frequency that the user does not realize this. For example, the information on the detector is maintained during at least a part of the image acquisition. According to a further example, the information is projected on the detector and the patient, at least during a part of the image acquisition. According to a further example, the graphical positioning information comprises instructions 66 related to the determined X-ray image acquisition. For example, this is shown in FIG. 5 exemplarily only. It must be noted that the feature of providing instructions, such as the instructions 66, is also provided for the other examples shown, in particular for the adaptable display surface 60, the e-paper coating structure 64, a light emitting structure as described below, the variation where the graphical positioning information is provided on a support surface, such as shown in FIG. 6, and/or also in combination with the projection of the graphical positioning information according to the examples shown in FIGS. 3 and 4.

According to a further example, the graphical positioning information provided by the adaptable display surface 60, e.g. in case of the e-paper coating structure 64 or the light emitting structure, is provided to a processing unit to calibrate out the coating structure, to compensate for the graphical content shown. In case of an alternating sequence of information provision and image acquisition, the calibrating of is not necessary. However, because of the thin layer and the more or less uniform structure, the coating can be easily calibrated out of the final image and does only consume a small fraction of the overall detector source.

The graphical positioning information 14 may also be provided in a visible frequency, i.e. for a short time in a repeated manner.

According to a further example, the instructions are provided for an interaction of a user. The visible surface 42 comprises areas or portions 68, which are activatable by the user for entering feedback upon the instructions.

For example, a number of capacity sensors are provided detecting a touch of the respective surface area 68.

For example, patients can be guided through the positioning procedure by providing the respective instructions.

For example, with an active e-paper coating or a light emitting structure, it is possible to visualize the patient identification, especially for emerging markets, entering the question "Am I the right one to be radiographed now?" It is further possible to visualize the examination information for the patient, such as type: "I am here for a broken foot", target organ outlines, "Where should I place my hand?", or specific requirements, e.g. inspiration, expiration "Should I hold my breath?". Further, examination information for the technician can be provided such as follow-up positioning: "How did I place the knee last time?", location of the AEC chambers: "Which chambers are active and where are they?", ALARA (As Low As Reasonably Achievable) for follow-up examinations: "How big is the patient's lung? How should I collimate?", laterality: "the left or the right hand first?", or required additional equipment: "Lead vest? Markers?".

Further, also system information could be provided, such as battery power remaining, connectivity, for example for a portable detector, avoiding LED structures. Also the number of examination or date since last calibration can be provided. Further, the position or geometry of the system can be provided.

By providing instructions to the patient, a throughput rate can be increased for many applications since positioning is provided, according to the present invention, in a self-explanatory manner to the examined patient.

According to the present invention, intelligent image pre-fetching and examination support is provided, for example by displaying patient-specific data of previous examinations or general anatomic target outlines, the active AEC chambers, and the like. The system calibration itself is kept unchanged. Also, the handling or portability is unchanged, since, in particular for an e-paper solution, no additional weight or wires are provided.

Depending on the embodiments of implementation, i.e. what kind of information to display, for each examination, the acquisition workstation (AWS) communicates patient identification, examination type, target organ outlines, and the like, to the detector via the same communication channel that is used for control signals (data is mostly textural or vector graphics and thus small in size) for the control of the adaptable display surface 60 or the projection 22.

According to a further exemplary embodiment of the present invention, an X-ray imaging system 70 is provided, comprising an X-ray source 72, such as, for example, the X-ray source 36 shown in FIGS. 3 and 4, or the X-ray source 58 shown in FIG. 6. Further, a guiding system 10 according to one of the above described examples is provided. For example, the X-ray imaging system 70 is also shown in FIGS. 3, 4, and 6 in different embodiments.

The X-ray source 72 is configured to radiate an X-ray beam towards the detector arrangement and the graphical positioning information 14 is provided for guiding in positioning a region of interest of a patient between the X-ray source 72 and the detector arrangement, for example the detector arrangement 12, for X-ray image acquisition.

For example, a tracking arrangement (not further shown) is provided for tracking position of the X-ray system components, and the projection arrangement is fixed. The projection is adapted according to the radiation direction of the X-ray system.

According to a further example, the adaptable display surface is light-emitting, as already indicated above.

Figure 8:
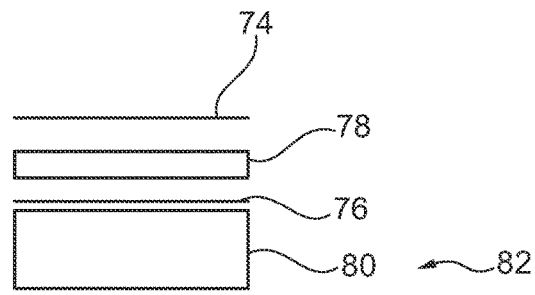
FIG. 8 shows a further example of an X-ray detector arrangement according to the present invention.

As shown in FIG. 8, a light-emitting layer 74 with at least one light-emitting element is arranged in front of a detector photodiode layer 76. In FIG. 8, a scintillator 78 is indicated as well as a support structure 80 for the detector photodiode layer. The scintillator 78 may be arranged behind the light-emitting layer 74, and, of course, in front of the detector photodiode layer 76. The latter and the support (or mounting) structure 80 are forming parts of a detector 82.

Figure 9:
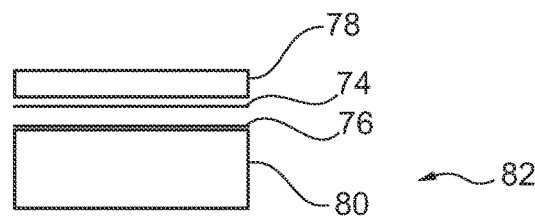
FIG. 9 shows a still further example of an X-ray detector arrangement according to the present invention.

According to a further example, shown in FIG. 9, the light-emitting layer 74 is arranged behind the scintillator 78, also referred to as scintillator layer 78.

Figure 10:
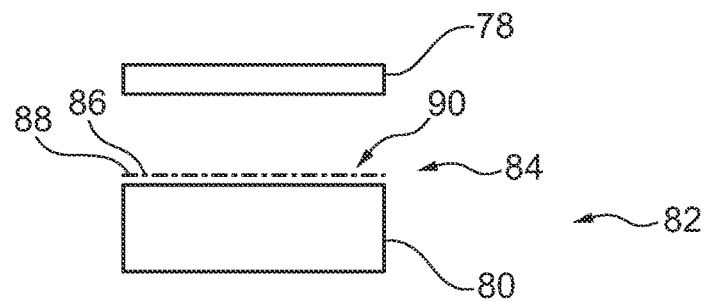
FIG. 10 shows another exemplary embodiment of an X-ray detector arrangement according to the present invention.

According to a further example, shown in FIG. 10, instead of having two different layers for the light-emitting function and the detector function, a mixed layer 84 is provided that, for example, is mounted or attached to the support structure 80. The mixed layer 84 comprises light-emitting elements 86 and detector photodiode elements 88, which are arranged in an interlaced pattern 90 to form the mixed layer 84. For example, the scintillator 78 is arranged in front of the mixed layer 84, as shown in the drawing.

When providing the scintillator layer 78 in front of the light-emitting elements, i.e. in front of the actual adaptable display surface—although the latter is not really forming the front surface of the arrangement, the scintillator layer is at least partly transparent for the emitted wavelength of the light-emitting layer, thus making the light visible to the user.

With respect to the use of organic materials, the above-mentioned functional mix may be provided in a matrix structure with, for example, TFT readout and/or active TFT control elements on transparent substrates, for example flexible foils or glass. As the key feature in relation with the organic material, the more or less transparent thin functional layer of the OLEDs on top of the photodiodes provides the additional function of providing graphical information, while still allowing X-ray image acquisition. The resulting sensitivity through the OLED layer to the detector is still good enough and in addition, the layout of the readout TFT (for detector) and the control TFT (for LED) could be aligned to have the same active area and then also the same area for emission/detection. A scintillator layer on top of both structures has to be, as mentioned above, at least partly transparent for the emitted wave length of the light-emitting layer. The spatial resolution of the display (and the intensity) is limited by the centre layer properties. However, the use of a wave length-shifter in the system could optimize the efficiency for emission and detection with respect to the absorption of the scintillator. The design of the spectral responsivity of the photodiode and the emission wavelength of the LED display could be optimized for a minimum interference, or also for optimized reset functionality and even for advanced calibration and correction methods by active "correction illumination". The wavelength selection would be depending on the use of the respective organic material.

According to a further example, not shown, the at least one light-emitting element is provided as a reset light source for a scintillator layer of the detector arrangement, for example for the scintillator 78. Thus, it is possible to reset the scintillator, for example after X-ray radiation and the detection of the respective signals by the detector elements.

The reset light source, i.e. the light-emitting element(s) may be provided in front of the scintillator, or behind the scintillator. It is noted that the terms "in front of" or "behind" are relating to the direction of the X-ray radiation from an X-ray source towards the detector.

Figure 11:
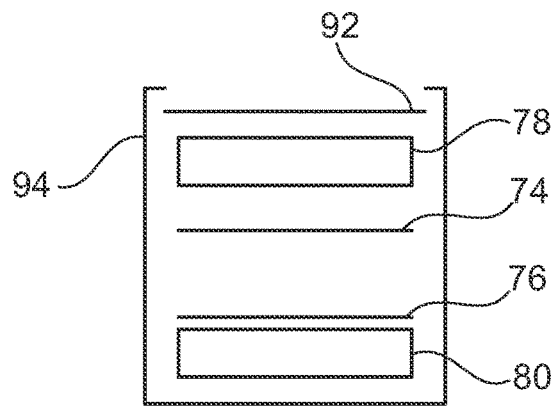
FIG. 11 shows a further example of an X-ray detector arrangement according to the present invention.

In case the light-emitting layer 74 is arranged behind the scintillator 78, the coupling of ambient light into the detector elements is prevented by providing a filter arrangement in front of the detector element. For example, a shielding layer 92 is provided in front of the scintillator layer 78, and an enclosing housing 94 is arranged around the respective stack of layers, as shown in FIG. 11.

According to a further example, the adaptable display surface is provided with an organic light-emitting diode (OLED) coating structure. An OLED structure can be used, for example, for detectors mounted and connected to an adaptable support, in particular.

According to an example (not further shown), the at least one light-emitting element is provided as an organic light-emitting diode OLED. For example, the light-emitting layer 74 is provided as an OLED layer.

However, according to a further example, the at least one light-emitting element may also be provided as a conventional LED.

Figure 12:
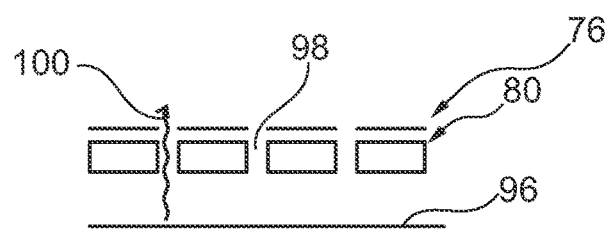
FIG. 12 shows an example of a light-emitting structure according to the present invention.

According to a further example, shown in FIG. 12, a background light source 96 of any kind is provided, and light-transmitting openings 98 are provided in the detector surface, i.e. in the support structure 80 as well as in the detector photodiode layer 76. Thus, at least for some locations, a light beam 100 is thus projected and thus visible to a user, a plurality forming the graphical positioning information.

The light openings may be provided to be controllable in order to adapt the displayed information. Further, alternative or in addition, the light source may be provided to be controllable or switchable for at least some portions of the display surface.

Figure 13:
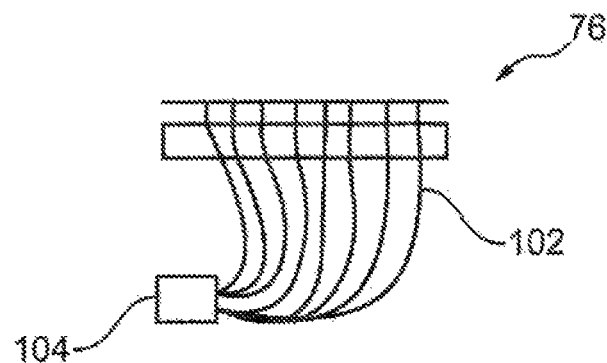
FIG. 13 shows a further example of a light-emitting structure according to the present invention.

According to a further example, shown in FIG. 13, the at least one light-emitting element may be provided by an arrangement of light-guiding elements 102 reaching from a light source 104 to the detector layer 76 or to a surface in front of the detector (not further shown) such as a detector cover.

The light-guiding elements may be provided with controllable element to regulate the output of light within the display surface. Further, as an alternative or in addition, the light source may be provided with respective controllable elements.

For example, the detector elements 88 are provided in an array structure and the light-emitting elements 86, also comprising the openings shown in FIG. 12 or the ends of the light-transmitting elements 102, such as glass fibre tables, are provided in a light pattern, wherein the light pattern is different from the array structure. For example, the array structure is covering a far higher number of image points, thus the light pattern having a larger grid structure providing a smaller resolution of the light elements, i.e. a smaller number of light points compared to the detector element points.

For example, OLEDs are printed onto a substrate. Thus, a continuous light-emitting layer, as described in FIGS. 8 and 9, as examples, may be provided while being X-ray transparent when printed onto an approximate substrate.

According to a further example, OLEDs and detector photodiode elements are printed onto a substrate in an interlaced manner, as described in principle with relation to FIG. 10.

According to a further example, the detector is configured to detect a reflected intensity from light provided by the light-emitting adaptable display surface and/or light provided by a visible light projection from a projection arrangement. The guiding system is further configured to determine an actual field of view after the positioning of an object. For example, the actual field of view can be provided for an optimized setting of shutters and/or optimized tube settings.

Figure 14:
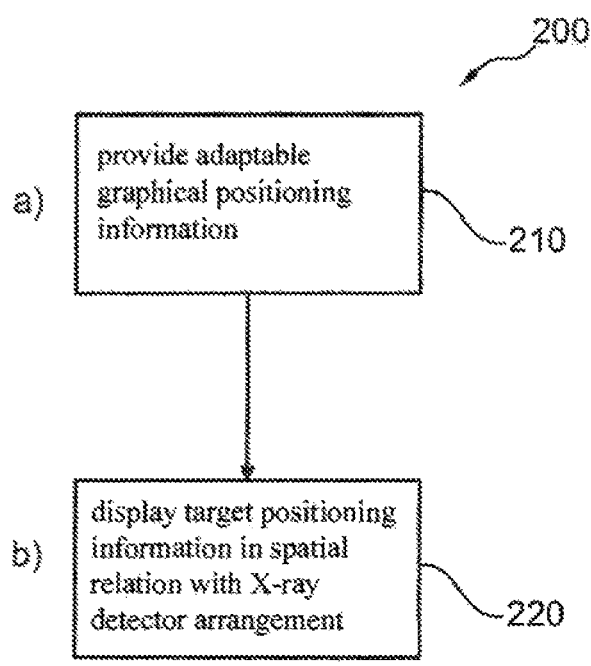
FIG. 14 shows basic steps of a method for guiding in positioning a region of interest of a patient for X-ray image acquisition according to an exemplary embodiment of the invention.

FIG. 14 shows a method 200 for guiding in position a region of interest of a patient for X-ray imaging acquisition. In a providing step 210, graphical positioning information is provided. The graphical positioning information comprises at least a graphical target anatomy representation. Further, in a displaying step 220, the graphical target positioning information is displayed in spatial relation with the X-ray detector arrangement. The graphical target anatomy representation indicates a target position of a respective anatomy of the patient for a determined X-ray image acquisition. The graphical positioning information is adaptable in accordance with the determined X-ray image acquisition.

The providing step 210 is also referred to as step a), and the displaying step 220 as step b).

According to a further example (not further shown), in step b), the graphical target anatomy representation is provided as a visible light projection in a projection direction towards the detector arrangement.

According to a still further example (also not further shown), in step b), the graphical positioning information is provided by an adaptable display surface on a visible surface of the X-ray detector arrangement.

In a further example, a combination of a visible light projection and an adaptable display surface is provided, e.g. a combination of the projector and the e-paper and/or the light-emitting surface.

As mentioned above, the adaptable display surface may be light-emitting. Thus, according to a further example, in step b), the graphical positioning information is provided by a light-emitting layer with at least one light-emitting element arranged in front of the detector photodiode layer. In a further example, in step b), the graphical positioning information is provided by light-emitting elements that are arranged in an interlaced pattern with detector photodiode elements as a mixed layer.

According to a further example of a method, before an image acquisition, a scintillator of the detector arrangement is being reset by the at least one light-emitting element.

Figure 15:
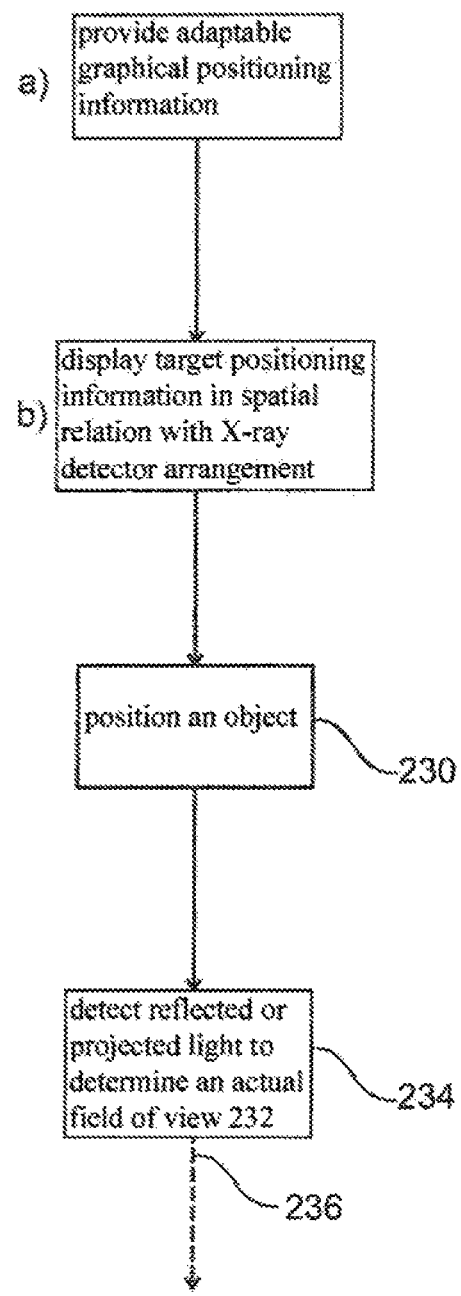
FIG. 15 shows a further example of a method according to the present invention.

According to a further example, shown in FIG. 15, after the positioning 230 of an object, an actual field of view 232 is determined by detecting 234 a reflected intensity from light provided by a light-emitting adaptable display surface, or a visible light projection from a projection arrangement. Thus, the knowledge of the actual field of view 232 may be provided for further purposes, as indicated with dotted arrow 236.

Figure 16:
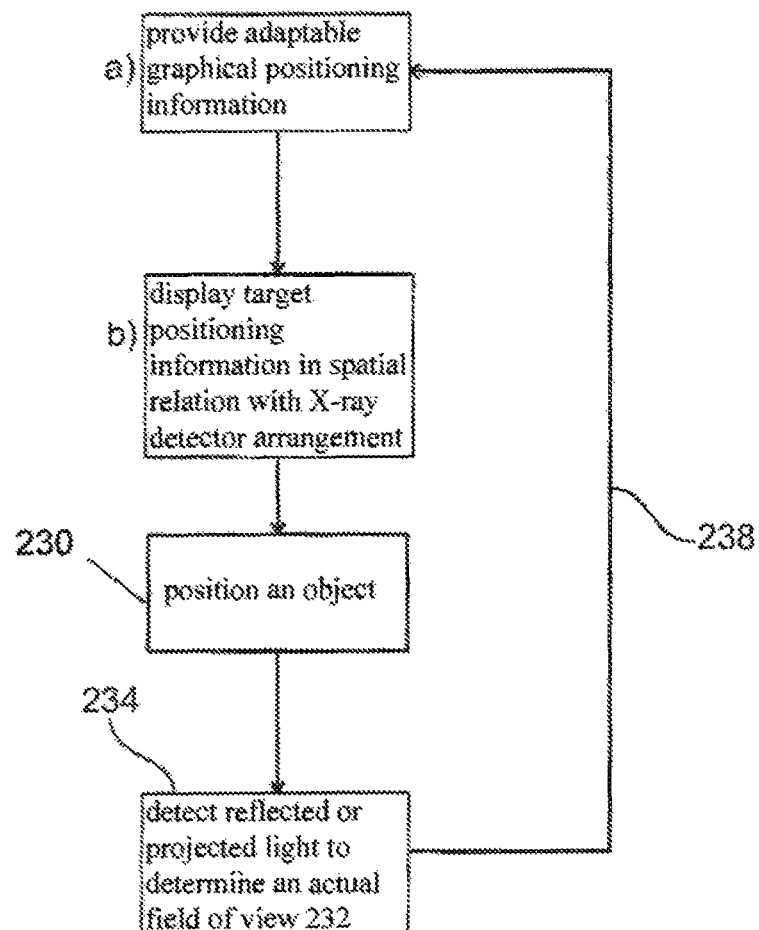
FIG. 16 shows a still further example of a method according to the present invention.

As shown in FIG. 16, the determined actual field of view 232 may be used 238 for adapting the graphical positioning information. Thus, an updated graphical target anatomy representation may be provided and displayed in steps a) and b).

For example, the display of the graphical positioning information to the user and the detection/determination of the actual field of view may be provided in an alternating switching manner, i.e. a sequence, which, when being fast enough, may be provided in such a way that it is not visible to the user. The user thus only notices a continuous adaption and improvement of the provided positioning information. The knowledge of the actual field of view, that could also be referred to as the actual field of interest, can also be used to optimize tube settings or also to optimize the shuttering arrangement, if available, in order to minimize the dose.

Further, a combination of displaying positioning information, including adapting the positioning information as described above, and image acquisition is provided in a sequential manner.

The present invention thus supports either a technician or a patient in guiding in position a region of interest of a patient for X-ray image acquisition. For example, to obtain optimal image quality in digital radiography and to meet the ALARA principle (As Low As Reasonably Achievable), the present invention provides for right patient positioning with respect to X-ray tube and detector. Further, especially for automatic exposure controlled examinations, to achieve proper detector dose independently of patient size and obesity, the requirements to place the patient's anatomy correctly with respect to the AEC measurement chambers is fulfilled. Further, for an optimal collimation of the X-ray beam, unnecessary exposure of the patient avoiding, the collimation of the X-ray beam can be correctly adjusted onto the targeted organ and thus displayed as positioning information.

According to the present invention, the indication of AEC chambers overcomes a number of disadvantages. The location of an AEC chamber may be drawn on the detector itself. However, the detector is typically either covered by the patient for wall examination, for example, or it is even hidden within the tray below the examination table for table acquisitions. Therefore, correct positioning with respect to the AEC chambers, as a challenging task that requires training and experience, is thus facilitated by the present invention. Thus, positioning errors in AEC examinations that lead to over- or under-exposure are prevented. Thus, the present invention aims at an optimal image quality for diagnostic purposes as well as matching the ALARA principle.

A further advantage is provided by the present invention, for example, in case of chest examinations where the target organ, for example the lung, is projected such that a user does not have to guess where the position of the target organ with respect to the projections is located.

According to a further example, a tube/detector positioning tracking is provided to compute the projection angle and distance to adapt the graphical positioning information respectively.

According to a first mode concerning the AEC chambers issue, the display model comprises the target anatomy and the AEC chambers optimally placed in it, the chamber's position with respect to the anatomy is fixed. The position of the display is linked to the actual AEC chamber position in front of the detector. The user has then to shift the patient so that the organ display coincides with the actual organ position.

According to a second mode, the model of the anatomy and the AEC chamber position are two independent displays. The display of the AEC chamber position is fixed by the detector position. The projection of the target anatomy is linked to the patient position only. The user in this case has to position the patient, so that the AEC chamber's display is well-placed compared to the organ projection.

For example, to implement both modes, the models of organ delineation for each type of examination are provided. Average anatomy models of each application are obtained, for example, via statistical shape modelling. In order to increase the granularity and better match with different patients, it is provided to derive different models for different populations, e.g. patient age, such as children, adults, BMI (body mass index) indices, such as normal or obese. The used projector can be of any kind to display on the patient the organ outlines as well as the AEC chamber (if used) and, for example, the collimator position.

From the known position and orientation of tube and detector, it is possible to derive or adapt the projection geometry. The target outlines are deformed such that they appear correctly on a detector, on the examination table or on the patient himself. Finally, the operator can toggle the visibility of outlines to support patient positioning.

When using a system capable of recording patient dimensions, according to an exemplary embodiment of the present invention, in a first mode, the mean target anatomy model is placed optimally according to the AEC chambers. This forms the template for patient positioning. For acquisitions without AEC, only the target organ outlines are projected in order to meet the requirements of a good acquisition and to achieve a standardized high image quality. In this mode, the system being able to record patient dimensions and position is not mandatory. If not available, the system can use the patient data (age, size, weight) entered by the user to choose the anatomy model adapted to the patient and to project it correctly. If an external system is available to measure patient body characteristics, the anatomy projection will be more accurate. Examples of such system can comprise a scales and a height gauge, for example.

In a second mode, the AEC chamber projection is fixed but the anatomy model projection is linked to the patient position. An external system able to register in real time the patient position is provided. An example of such system can comprise two video cameras registering the scene from two different positions. Patient height, width, and thickness are then automatically recorded to adjust the organ model projections to the patient. The position of the patient is also tracked by the cameras in order to be able to project the model on his/her skin at the location of the underlying target organ.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging guiding system for positioning a patient for X-ray image acquisitions, comprising:
   an X-ray detector arrangement;
   and
   a controller configured to provide graphical positioning information in spatial relation with the X-ray detector arrangement,
   wherein the graphical positioning information comprises a graphical target anatomy representation,
   wherein the graphical target anatomy representation indicates a target position of an underlying target organ of the patient for a determined X-ray image acquisition, and
   wherein the controller is further configured to link the target position to a patient position of the patient to change the target position with a movement of the patient and present the target position at a location of the underlying target organ.

2. The X-ray imaging guiding system according to claim 1, further comprising a projection arrangement configured to project visible light, and wherein the graphical target anatomy representation is provided as a visible light projection in a projection direction towards the detector arrangement.

3. The X-ray imaging guiding system according to claim 2, wherein the graphical positioning information comprises a target indicator indicating a predetermined area of the X-ray detector, and wherein the graphical target anatomy representation and the target indicator are provided in a predetermined spatial relation.

4. The X-ray imaging guiding system according to claim 2, wherein a patient positioning arrangement is provided detecting the movement of the patient, wherein the graphical target anatomy representation is linked to the movement of the patient, wherein a target indicator is provided indicating a predetermined area of the X-ray detector, and wherein the graphical target anatomy representation and the target indicator can be brought into a determined spatial relation through the respective motion of the X-ray detector arrangement and the patient in relation to each other.

5. The X-ray imaging guiding system according to claim 1, wherein the X-ray detector arrangement comprises a visible surface configured to be located in an X-ray radiation beam during the X-ray image acquisition;
wherein the graphical positioning information is provided on the visible surface; and
wherein the visible surface is provided at least as one of the group of: i) a detector cover; ii) a patient support surface; or iii) a patient abutting surface.

6. The X-ray imaging guiding system according to claim 5, wherein the visible surface comprises an adaptable display surface.

7. The X-ray imaging guiding system according to claim 6, wherein the adaptable display surface is provided with an e-paper coating structure.

8. The X-ray imaging guiding system according to claim 6, wherein the adaptable display surface is light emitting; and
wherein a light emitting layer with at least one light emitting element is arranged in front of a detector photodiode layer.

9. The X-ray imaging guiding system according to claim 8, wherein the at least one light emitting element is provided as an organic light-emitting diode.

10. The X-ray imaging guiding system according to claim 8, wherein the at least one light emitting element is provided as a reset light source for a scintillator of the X-ray detector arrangement.

11. The X-ray imaging guiding system according to claim 6, wherein the adaptable display surface is light emitting; and
wherein light emitting elements and detector photodiode elements are arranged in an interlaced pattern as a mixed layer.

12. The X-ray imaging guiding system according to claim 5, wherein the graphical positioning information comprises instructions related to the determined X-ray image acquisition;
wherein the instructions are provided for an interaction of a user; and
wherein the visible surface comprises areas or portions (68) which are activatable by the user for entering feedback upon the instructions.

13. The X-ray imaging guiding system according to claim 1, wherein the graphical positioning information is maintained during an X-ray imaging procedure.

14. An X-ray imaging system, comprising:
an X-ray source; and
a guiding system according to claim 1;
wherein the X-ray source is configured to radiate an X-ray beam towards the X-ray detector arrangement; and
wherein the graphical positioning information is provided for guiding in positioning a region of interest of the patient between the X-ray source and the X-ray detector arrangement for X-ray image acquisition.

15. The X-ray imaging guiding system of claim 1, wherein the graphical positioning information further comprises a target indicator indicating a predetermined area of the X-ray detector, and wherein a location of the target indicator remains fixed while the target position of the patient changes with the movement of the patient.

16. A method for guiding in positioning a region of interest of a patient for X-ray image acquisition, comprising acts of:
providing graphical positioning information comprising a graphical target anatomy representation;
displaying the graphical target anatomy representation in spatial relation with an X-ray detector arrangement, wherein the graphical target anatomy representation indicates a target position of an underlying target organ of the patient for a determined X-ray image acquisition;
linking the target position to a patient position of the patient to move the target position with a movement of the patient; and
presenting the target position at a location of the underlying target organ.

17. The method according to claim 16, wherein in the displaying act, the graphical target anatomy representation is provided as a visible light projection in a projection direction towards the X-ray detector arrangement.

18. The method according to claim 16, wherein in the displaying act, the graphical positioning information is provided by an adaptable display surface on a visible surface of the X-ray detector arrangement, wherein after positioning of the region of interest of the patient, an actual field of view is determined by detecting a reflected intensity from light provided by a light emitting adaptable display surface.

19. A non-transitory computer-readable medium comprising computer instructions for guiding in positioning a region of interest of a patient for X-ray image acquisition which, when executed by a processor, configure the processor to perform acts of:
providing graphical positioning information comprising a graphical target anatomy representation;
causing display of the graphical target anatomy representation in spatial relation with an X-ray detector arrangement, wherein the graphical target anatomy representation indicates a target position of an underlying target organ of the patient for a determined X-ray image acquisition;
linking the target position to a patient position of the patient to move the target position with a movement of the patient; and
causing presentation of the target position at a location of the underlying target organ.

\* \* \* \* \*